United States Patent
Bradley (10) Patent No.: US 7,911,315 B2
(45) Date of Patent: Mar. 22, 2011

(54) MINIATURE PRESSURE SENSOR ASSEMBLY FOR CATHETER

(75) Inventor: Alistair D. Bradley, Dublin, OH (US)

(73) Assignee: Honeywell International Inc., Morristown, NJ (US)

(*) Notice: Subject to any disclaimer, the term of this patent is extended or adjusted under 35 U.S.C. 154(b) by 630 days.

(21) Appl. No.: 11/496,533

(22) Filed: Jul. 28, 2006

(65) Prior Publication Data

US 2008/0027332 A1    Jan. 31, 2008

(51) Int. Cl.
| | |
|---|---|
| A61B 5/103 | (2006.01) |
| A61B 5/117 | (2006.01) |
| G01B 5/30 | (2006.01) |
| G01B 7/16 | (2006.01) |
| H01L 27/108 | (2006.01) |
| H01L 29/94 | (2006.01) |
| G01L 1/22 | (2006.01) |
| H01C 10/10 | (2006.01) |

(52) U.S. Cl. ........... 338/2; 600/587; 73/760; 73/763; 73/777; 73/780; 73/781; 257/301; 257/302; 257/303; 338/47

(58) Field of Classification Search ............ 600/587; 73/760, 763, 777, 780, 781; 257/301–303; 338/2–6, 36, 37, 42, 47

See application file for complete search history.

(56) References Cited

U.S. PATENT DOCUMENTS

| | | | | |
|---|---|---|---|---|
| 2,344,642 | A * | 3/1944 | Ruge | 338/3 |
| 4,274,423 | A | 6/1981 | Mizuno et al. | 128/675 |
| 4,481,497 | A * | 11/1984 | Kurtz et al. | 338/2 |
| 4,622,856 | A * | 11/1986 | Binder et al. | 73/727 |
| 4,722,348 | A | 2/1988 | Ligtenberg et al. | 128/675 |
| 4,782,319 | A * | 11/1988 | Dell'Acqua et al. | 338/4 |
| 4,809,704 | A | 3/1989 | Sogawa et al. | 128/675 |
| 4,864,271 | A * | 9/1989 | Yajima | 338/4 |
| 4,991,283 | A * | 2/1991 | Johnson et al. | 29/595 |
| 5,050,297 | A | 9/1991 | Metzger | 29/855 |
| 5,107,710 | A * | 4/1992 | Huck et al. | 73/708 |
| 5,142,915 | A * | 9/1992 | Bergstrom | 73/727 |
| 5,201,228 | A * | 4/1993 | Kojima et al. | 73/724 |
| 5,465,626 | A * | 11/1995 | Brown et al. | 73/715 |
| 5,896,090 | A * | 4/1999 | Okada et al. | 340/667 |
| 5,901,046 | A * | 5/1999 | Ohta et al. | 361/760 |

(Continued)

OTHER PUBLICATIONS

Wymyslowski A et al., Sequential Approach to Numerical Optimization of the LTCC Ceramic Pressure Sensor, 6th Int'l Conf., IEEE, Apr. 2005, USA, pp. 376-383.

*Primary Examiner* — Max Hindenburg
*Assistant Examiner* — Sean P Dougherty (57) ABSTRACT

A pressure sensor assembly configured for use with a catheter. In one illustrative embodiment, the pressure sensor assembly may include a multi-layer co-fired ceramic (MLCC) package. The MLCC package may include two or more ceramic layers that are co-fired together, with a cavity defined by at least some of the ceramic layers. At least one internal bond pad is provided within the cavity, and at least one external connection point is provided on the MLCC package exterior. A sensor, such as a pressure sensor, may be positioned and attached within the cavity. The sensor may be electrically connected to at least one of the internal bond pads. In some cases, a sealant may be used to encapsulate the sensor within the cavity. Once fabricated, the MLCC sensor assembly may be provided in a sensor lumen of a catheter.

20 Claims, 8 Drawing Sheets

U.S. PATENT DOCUMENTS

| | | | |
|---|---|---|---|
| 5,902,248 A | 5/1999 | Millar et al. | 600/485 |
| 6,146,743 A | 11/2000 | Haq et al. | 428/210 |
| 6,272,928 B1* | 8/2001 | Kurtz | 73/721 |
| 6,379,988 B1 | 4/2002 | Peterson et al. | |
| 6,384,473 B1 | 5/2002 | Peterson et al. | |
| 6,394,986 B1 | 5/2002 | Millar | 604/264 |
| 6,531,341 B1* | 3/2003 | Peterson et al. | 438/123 |
| 6,546,822 B1* | 4/2003 | Tahara et al. | 73/862.41 |
| 6,604,429 B1* | 8/2003 | Pitzer | 73/756 |
| 6,632,265 B1* | 10/2003 | Mukuno et al. | 75/739 |
| 6,999,818 B2 | 2/2006 | Stevenson et al. | 607/37 |
| 7,007,553 B2* | 3/2006 | Kinoshita et al. | 73/777 |
| 7,041,057 B1* | 5/2006 | Faupel et al. | 600/365 |
| 7,072,713 B2* | 7/2006 | O'Phelan et al. | 607/10 |
| 7,460,898 B2* | 12/2008 | Brister et al. | 600/347 |
| 7,467,003 B2* | 12/2008 | Brister et al. | 600/347 |
| 7,506,548 B2* | 3/2009 | Fukuda et al. | 73/756 |
| 2003/0102502 A1* | 6/2003 | Togashi | 257/303 |
| 2004/0106857 A1* | 6/2004 | Gough | 600/345 |
| 2004/0147960 A1* | 7/2004 | O'Phelan et al. | 607/1 |
| 2004/0147961 A1* | 7/2004 | O'Phelan et al. | 607/1 |
| 2004/0183147 A1* | 9/2004 | Togashi et al. | 257/414 |
| 2005/0073040 A1 | 4/2005 | Lee et al. | |
| 2006/0005631 A1* | 1/2006 | Hashimoto et al. | 73/780 |
| 2006/0091494 A1* | 5/2006 | Miyamoto et al. | 257/532 |
| 2007/0173711 A1* | 7/2007 | Shah et al. | 600/347 |
| 2008/0078251 A1* | 4/2008 | Fukuda et al. | 73/756 |

* cited by examiner

MINIATURE PRESSURE SENSOR ASSEMBLY FOR CATHETER

TECHNICAL FIELD

Embodiments relate to sensors, pressure sensors, and sensor systems. Embodiments also relate to semiconductor packaging, ceramic packaging, and multi-layer co-fired ceramics. Embodiments additionally relate to catheters and medical instrumentation.

BACKGROUND OF THE INVENTION

Sensors, such as pressure sensors can be placed near the tip of a catheter. Prior art instrumented catheters include those claimed in U.S. Pat. No. 5,902,248, U.S. Pat. No. 4,274,423, U.S. Pat. No. 6,394,986, U.S. Pat. No. 5,050,297, U.S. Pat. No. 4,809,704, and U.S. Pat. No. 4,722,348 that are herein included by reference in their entirety.

The current art catheters, however, can be expensive, lack measurement fidelity, be complex to set-up and/or require cleaning, sterilization & maintenance between uses. For example, reusable catheters cost around $1000 while single use fluid-filled catheters with low enough cost to be disposable can lack performance. Systems and techniques for producing instrumented catheters that are inexpensive are needed. Aspects of the embodiments directly address the shortcomings of current technology by using packaging technologies that can be used in mass production. A further benefit is that the advanced packaging leads to sensors that are more robust than those used in the current art.

BRIEF SUMMARY

The following summary is provided to facilitate an understanding of some of the innovative features unique to the embodiments and is not intended to be a full description. A full appreciation of the various aspects of the embodiments can be gained by taking the entire specification, claims, drawings, and abstract as a whole.

It is therefore an aspect of the embodiments to produce a multilayer co-fired ceramic (MLCC) package with a cavity into which a sensor can be placed. The sensor is electrically connected to internal bond pads within the cavity. Internal interconnects, corresponding to leads, traces, and/or vias, electrically connect the internal bond pads to external connection points on the outside of the MLCC package.

MLCC packages can be formed using a variety of different materials. MLCC packages formed with an aluminium oxide substrate (alumina) are often called High Temperature Co-fired Ceramic (HTCC) packages. Low Temperature Co-fired Ceramic (LTCC) packages are MLCCs based upon substrate materials with mixtures of glass and ceramic powders in binders and organic solvents to allow lower firing temperatures.

Typically, layers of ceramic material are formed, processed, stacked (laminated), and fired. After forming, a layer of ceramic material is produced. Processing includes operations such as forming holes and printing metal traces. The holes can be metallized to form electrical interconnects that pass through the layer of ceramic materials. Feed through and passages can be produced by processing holes and channels into ceramic layers. Air can pass through a passage. A wire can pass through a feed through. After processing multiple ceramic layers can be stacked and fired to produce a MLCC. Those practiced in the art of ceramic packaging know of these and many other operations that are used in the formation of MLCC packages.

It is also an aspect of the embodiments to produce a MLCC sensor assembly by placing a sensor into the cavity, electrically connecting the sensor to the internal bond pads, and sealing the sensor within the cavity. Those practiced in the art of semiconductor packaging or ceramic packaging are familiar with connecting to bond pads and sealing packages.

For example, the sensor can be attached, wire bonded, and sealed. A sensor can be attached by dispensing die attach adhesive and then positioning the sensor. Passages for reference air pressure or wiring must be kept open during attachment. Standard wire bonding techniques and equipment can be used to produce the electrical attachments between the sensor and the package. Finally, standard sealants, such as silicones, epoxy or glop top can be used to encapsulate the sensor within the package.

It is a further aspect of the embodiments to place the MLCC sensor assembly into one lumen of a catheter having one or more lumen. Many catheters have a single passageway leading from one end of the catheter to the other. Other catheters have multiple passageways. As such, the MLCC sensor assembly can be positioned inside one lumen of a catheter. The lumen containing the MLCC sensor assembly can be called the sensor lumen. An electrical connection can be established with the MLCC sensor assembly by attaching wires, such as those in a ribbon cable, to the MLCC sensor assembly. For example, the wires at one end of a ribbon cable can be connected to a MLCC sensor assembly's external connection points. The assembly can then be inserted into a lumen and fixed into position. The ribbon cable can then be used to establish electrical connections to the MLCC sensor assembly.

It is an aspect of certain embodiments to position more than one MLCC sensor assembly in a lumen. Wires can pass under or around one MLCC sensor assembly in order to reach a second MLCC sensor assembly. For example, two MLCC sensor assemblies can be electrically connected to different places on a single ribbon cable. The sensors and cable can then be fixed into position in a lumen. Obviously, each sensor assembly can alternatively have a dedicated cable.

It is an aspect of some embodiments that the sensor is a pressure sensor. As such, pressure external to the catheter must reach the sensor. A flexible sealant that transmits pressure can be used or a hole can pass through the catheter wall and sealant to reach the pressure sensor membrane directly. Some pressure sensors require a reference input. A passage through the MLCC package can allow reference media from within the catheter lumen (e.g. vented to atmospheric air) to reach the pressure sensor's reference input. The passage and the pressure sensor reference input must be aligned within the cavity. For example air can pass through the sensor lumen, through the passage, and to the pressure sensor.

BRIEF DESCRIPTION OF THE DRAWINGS

The accompanying figures, in which like reference numerals refer to identical or functionally similar elements throughout the separate views and which are incorporated in and form a part of the specification, further illustrate aspects of the embodiments and, together with the background, brief summary, and detailed description serve to explain the principles of the embodiments.

DETAILED DESCRIPTION

The particular values and configurations discussed in these non-limiting examples can be varied and are cited merely to illustrate at least one embodiment and are not intended to limit the scope thereof. In general, the figures are not to scale.

A batch fabricated miniature pressure sensor assembly provides a ceramic substrate with cavity to allow sealing and alignment of die to a reference hole/cavity. The assembly offers mechanical protection to wire bonds and die and provides an area for containing protective & isolating encapsulant, such as RTV or silicone, with good control of coating thickness above the pressure membrane.

An electronic catheter containing a MLCC sensor assembly in a lumen provides many advantages. The MLCC package can have a reference hole linking to a channel that is buried or on bottom layer of the package to provide venting or a reference input to a pressure sensor. A channel passing completely through the assembly can provide a path for reference air to a second sensor positioned further into the catheter. An ultraminiature assembly is designed to be capable of fitting inside 6 French catheter with two lumen. One lumen is used for the sensor assembly, wires and reference pressure while the second can be used for other purposes such as a fluid fill lumen in Urology. The MLCC package allows forming connections to standard miniature pressure die using standard automated techniques such as wire bonding. Larger external connection points on the MLCC package allow ease of connection to catheter wires or to micro-ribbon cables.

Figure 1:
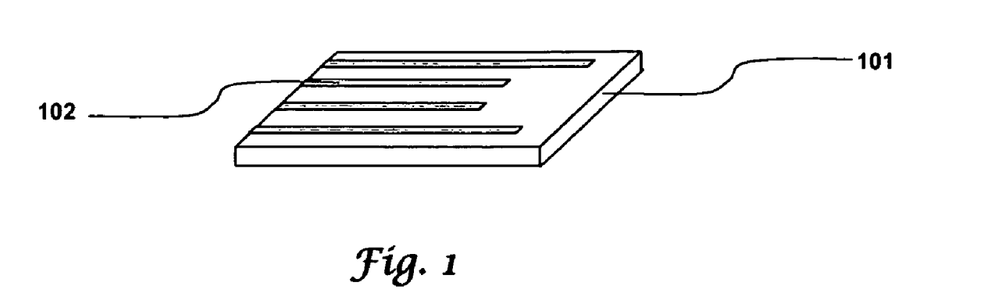
FIG. 1 shows an illustrative ceramic layer with traces, which may be used in some illustrative embodiments of a MLCC package.

FIG. 1 illustrates a ceramic layer 101 with traces 102 in accordance with aspects of the embodiments. In producing a MLCC package, ceramic slurry can be used to form ceramic layers. The layers are then processed. In processing, traces can be printed on the layer. The printed traces become metal traces during firing.

Figure 2:
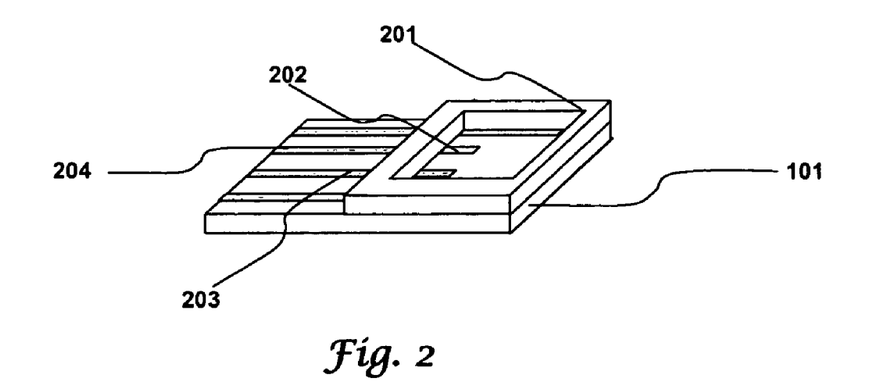
FIG. 2 shows the illustrative ceramic layer of FIG. 1 with an additional ceramic layer forming a cavity, which may be used in some illustrative embodiments of a stepped MLCC package.

FIG. 2 illustrates a stepped MLCC package in accordance with aspects of the embodiments. A first ceramic layer 201 is stacked on ceramic layer 101. The traces originally printed on the ceramic layer 101 become internal bond pads 202, internal interconnects 203 and external electrical connection points 204. The package is called "stepped" because the ceramic layers 101 and 201 do not all have the same dimensions.

Figure 3:
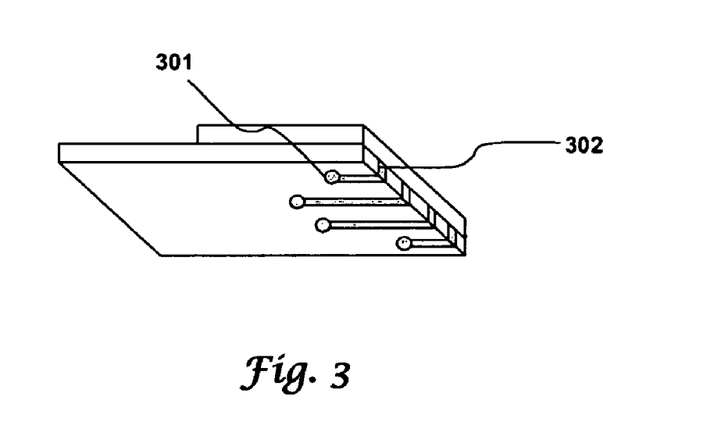
FIG. 3 shows two illustrative ceramic layers similar to that shown in FIG. 2 with via holes, which may be used in some illustrative embodiments of a MLCC package.

FIG. 3 illustrates a stepped MLCC package with via holes 301 in accordance with aspects of the embodiments. A hole through the ceramic layer can be metallized to form an internal electrical interconnect connecting an internal bond pad to an external trace or external connection point 302.

Figure 4:
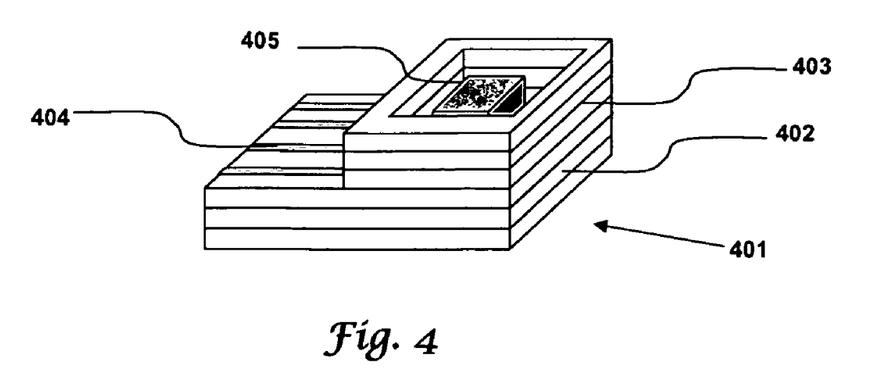
FIG. 4 shows a sensor attached in the cavity of an illustrative stepped MLCC package.

FIG. 4 illustrates a sensor 405 in the cavity of a stepped MLCC package in accordance with aspects of the embodiments. For ease of processing the MLCC package 401 is formed from six ceramic layers of equal thickness. The stepped package has the lower layers 402 being longer than other upper layers 403. The upper layers 403 form a cavity into which a sensor 405 is placed. One or more of the lower layers have been processed to provide internal bond pads, internal interconnects, and external connection points 404.

Figure 5:
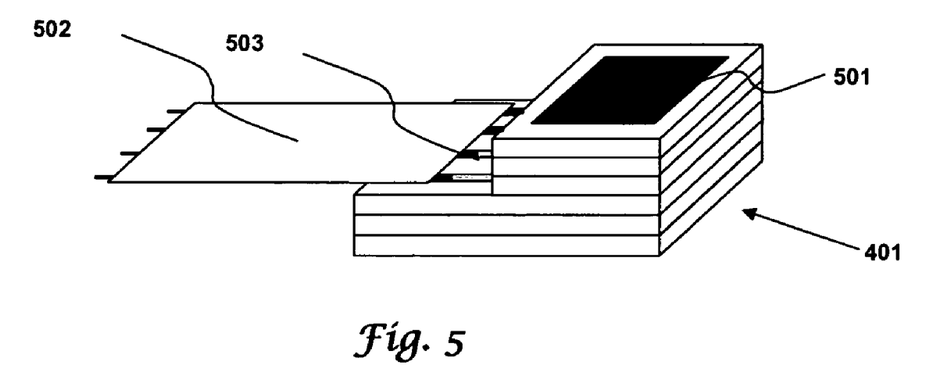
FIG. 5 shows a sensor encapsulated within the illustrative stepped MLCC package of FIG. 4, with an illustrative ribbon cable connection.

FIG. 5 illustrates a sensor encapsulated within a stepped MLCC package 401 with a miniature ribbon cable 502 in accordance with aspects of the embodiments. FIG. 5 is similar to FIG. 4 with the exceptions that encapsulant 501 now covers the sensor and a ribbon cable 502 is attached by connecting its wires 503 to the external connection points. An adhesive can be used to attach the cable to the MLCC package and thereby provide strain relief.

Figure 6:
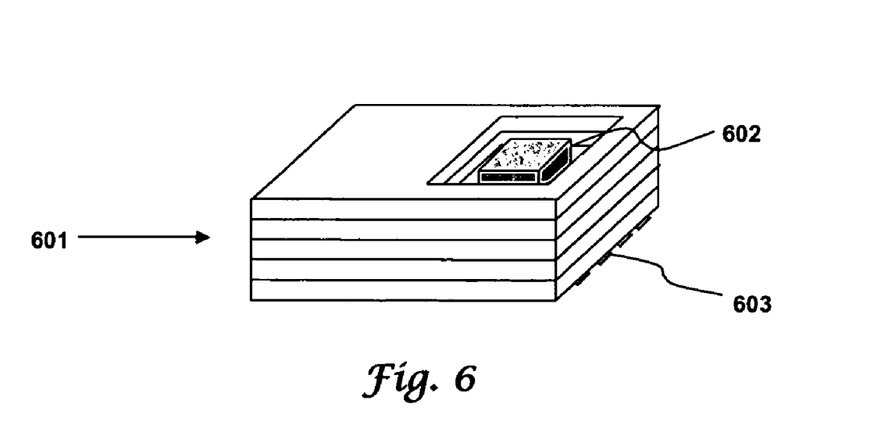
FIG. 6 shows a sensor attached in the cavity of another illustrative MLCC package.

FIG. 6 illustrates a sensor 602 in the cavity of a MLCC package 601 in accordance with aspects of the embodiments. Metallized holes, such as those of FIG. 3, connect the internal bond pads to the internal interconnects. The internal interconnects pass between ceramic layers to the external electrical connection points 603 on the base of the package. The sensor 602 can be electrically connected to the interior bond pads using standard semiconductor packaging techniques.

Figure 7:
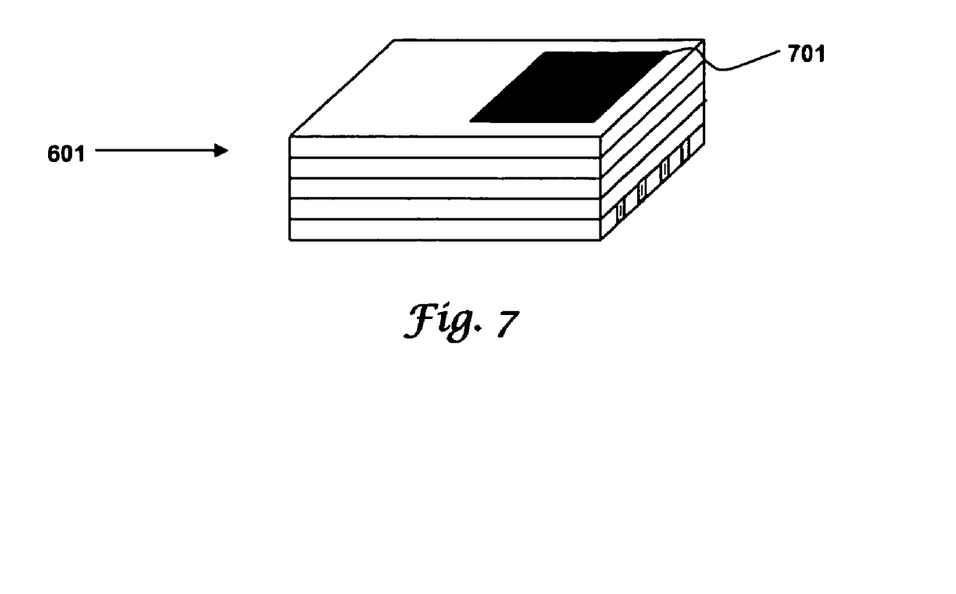
FIG. 7 shows a sensor sealed within the cavity of an illustrative MLCC package that is similar to the MLCC package shown in FIG. 6.

FIG. 7 illustrates a sensor sealed within the cavity of a MLCC package 601 in accordance with aspects of the embodiments. FIG. 7 is similar to FIG. 6 with the exception that encapsulant 701 is isolating the sensor within the package 601.

Figure 8:
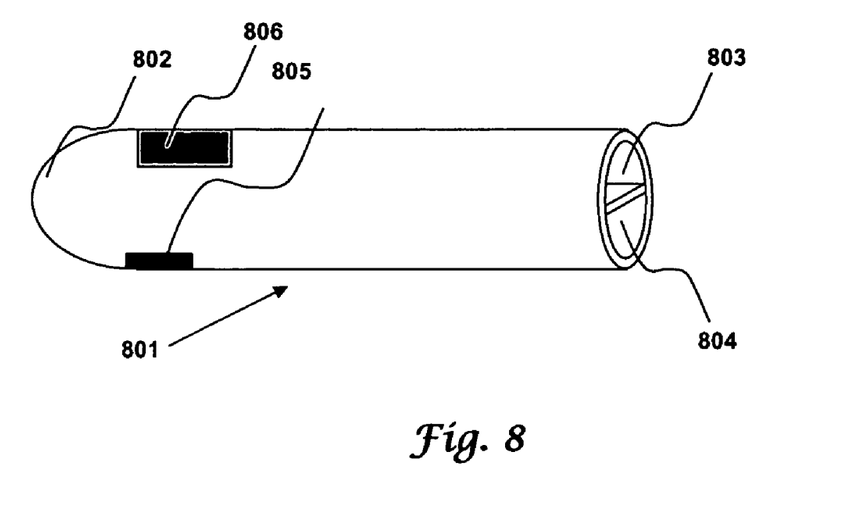
FIG. 8 illustrates an illustrative catheter with two lumen and a hole.

FIG. 8 illustrates a catheter 801 with two lumen and holes in accordance with aspects of the embodiments. The catheter 801 has a rounded end 802 and an open end revealing the two lumen. The bottom lumen 804 proceeds through the catheter to a bottom hole 805 such that fluid can flow through the lumen. The top lumen 803 proceeds through the catheter to a top hole 806. The top hole 806 is shaded grey to indicate MLCC sensor assembly positioning. If the catheter has large enough lumen a MLCC sensor assembly can be positioned by pushing it completely through the top lumen 803 toward the rounded end 802 in which case the top hole 806 need only be the size of the sensing surface. A MLCC sensor assembly can also be positioned by placing it through the top hole 806. A MLCC sensor assembly can also be located in the top hole 806 by pre-assembling a ribbon cable to the MLCC sensor assembly, threading the ribbon cable through the top hole 806 and top lumen 803, and using the ribbon cable to locate the MLCC sensor assembly into place in the top hole 806. The top hole 806 can then be sealed to fasten the MLCC sensor assembly in place and prevent fluid from flowing past the assembly. As such, reference air is allowed to reach the backside of the sensor from the top lumen 803, while the top-side is exposed to the external fluid only at the sensing surface.

Figure 9:
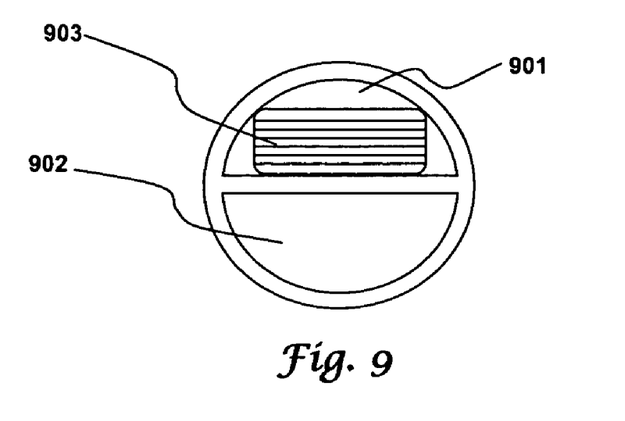
FIG. 9 illustrates a MLCC sensor assembly, such as that shown in FIG. 5 or 7, positioned and attached in a sensor lumen of a catheter, such as the catheter of FIG. 8.

FIG. 9 illustrates a MLCC sensor assembly 903 in a catheter in accordance with aspects of some embodiments. The catheter has a top lumen 901, holding the MLCC sensor assembly 903, and a bottom lumen. Notice that the MLCC sensor assembly has removed or rounded edges. The removed or rounded edges can ease the process of positioning of the MLCC assembly 903 within the top lumen 901.

Figure 10:
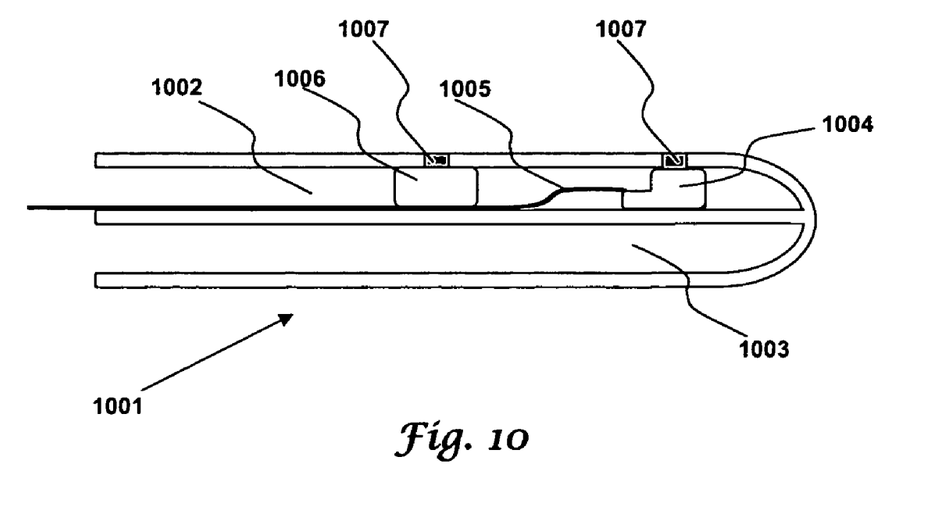
FIG. 10 illustrates a cutaway view of an illustrative catheter with two MLCC sensor assemblies.

FIG. 10 illustrates a cutaway view of a catheter 1001 with two MLCC sensor assemblies in accordance with aspects of some embodiments. The catheter 1001 has a bottom lumen 1003 and a top lumen 1002. The top lumen 1002 is used as the sensor lumen. A first MLCC sensor assembly 1004 is attached to a ribbon cable 1005 that passes under a second MLCC sensor assembly 1006. The second MLCC sensor assembly can also be attached to the ribbon cable 1005 to form electrical connections or have its own ribbon cable or other such miniature wires. The MLCC sensor assemblies can sense the outside environment through holes 1007 in the catheter.

Figure 11:
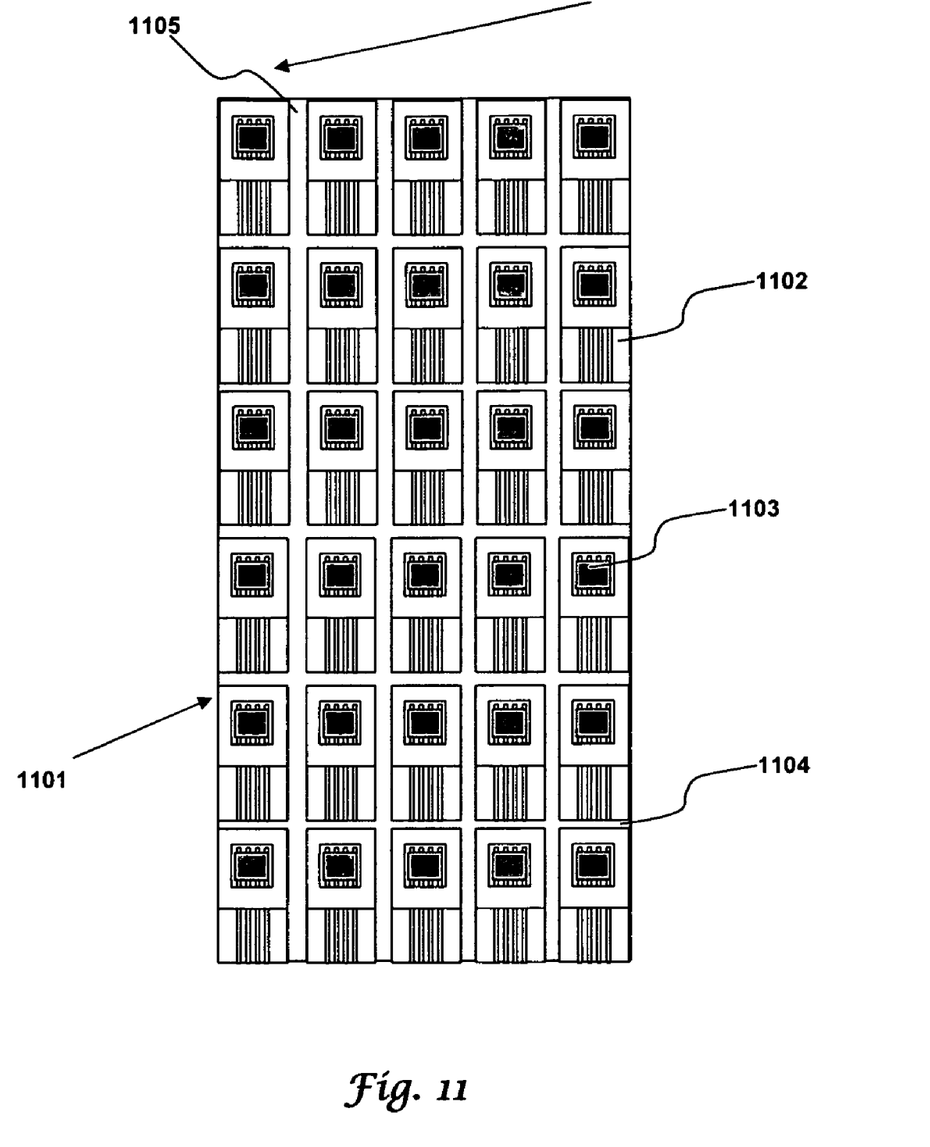
FIG. 11 illustrates a batch of stepped MLCC packages similar to that shown in FIG. 5, containing sensors in a single sheet prior to singulation.

FIG. 11 illustrates a sheet 1101 of stepped MLCC packages 1102 in a batch containing sensors 1103 prior to singulation in accordance with aspects of the embodiments. Those practiced in the art of semiconductor packaging know that ceramic packages can be produced in bulk in the form of sheets. The sheets can be split into individual packages by breaking, cutting, or otherwise separating the sheets along horizontal cut lines 1104 and vertical cut lines 1105. Rounded edges shown in FIG. 9 can be produced by pre-scoring of the ceramic sheet before firing or making additional cuts (e.g. v-shape) prior to singulation, or also by mechanical processing after singulation.

Figure 12:
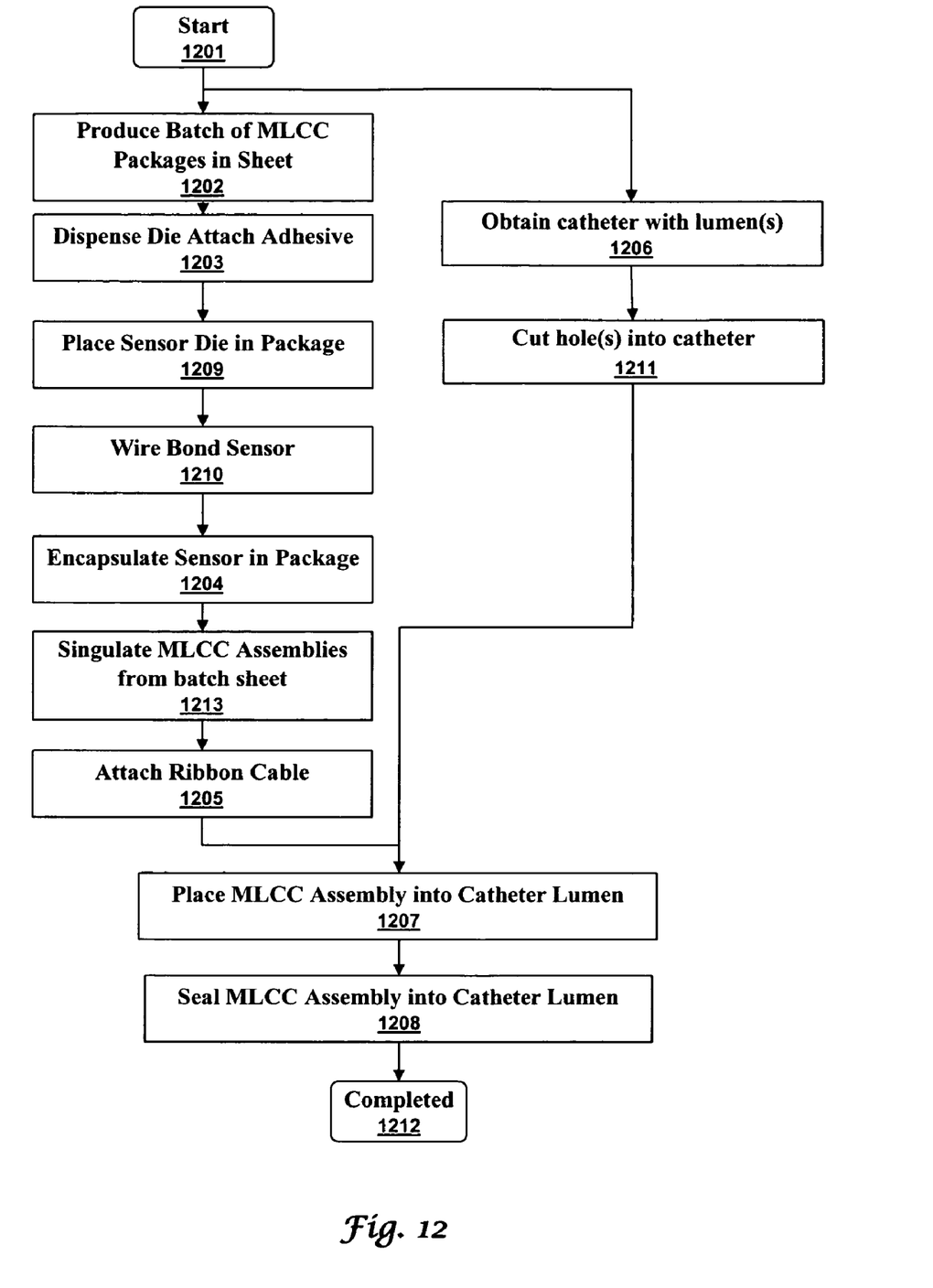
FIG. 12 illustrates a high level flow diagram of producing a catheter containing a MLCC sensor assembly.

FIG. 12 illustrates a high level flow diagram of producing a catheter containing a MLCC sensor assembly in accordance with aspects of the embodiments. After the start 1202 the process path branches. On one branch, a catheter is obtained 1206 and holes formed 1211 if required. On the other branch a batch of MLCC packages are produced 1202, die attach adhesive is dispensed 1203, and sensors bonded into the package 1209. Wire bonding 1210 electrically attaches the sensor to the internal bond pads and then the sensor is encapsulated in the package cavity 1204. Singulation from the batch MLCC sheet 1213 creates individual sensor assemblies. A ribbon cable is attached 1205 to the packages external connection points. Optionally at step 1213 the batch sheet could be only partially singulated forming horizontal strips so that ribbon cable can be attached in strips along one edge prior complete singulation. Finally the individual sensor assembly is positioned into a catheter lumen 1207 before the assembly is sealed into place 1208 and the process is complete 1212.

Figure 13:
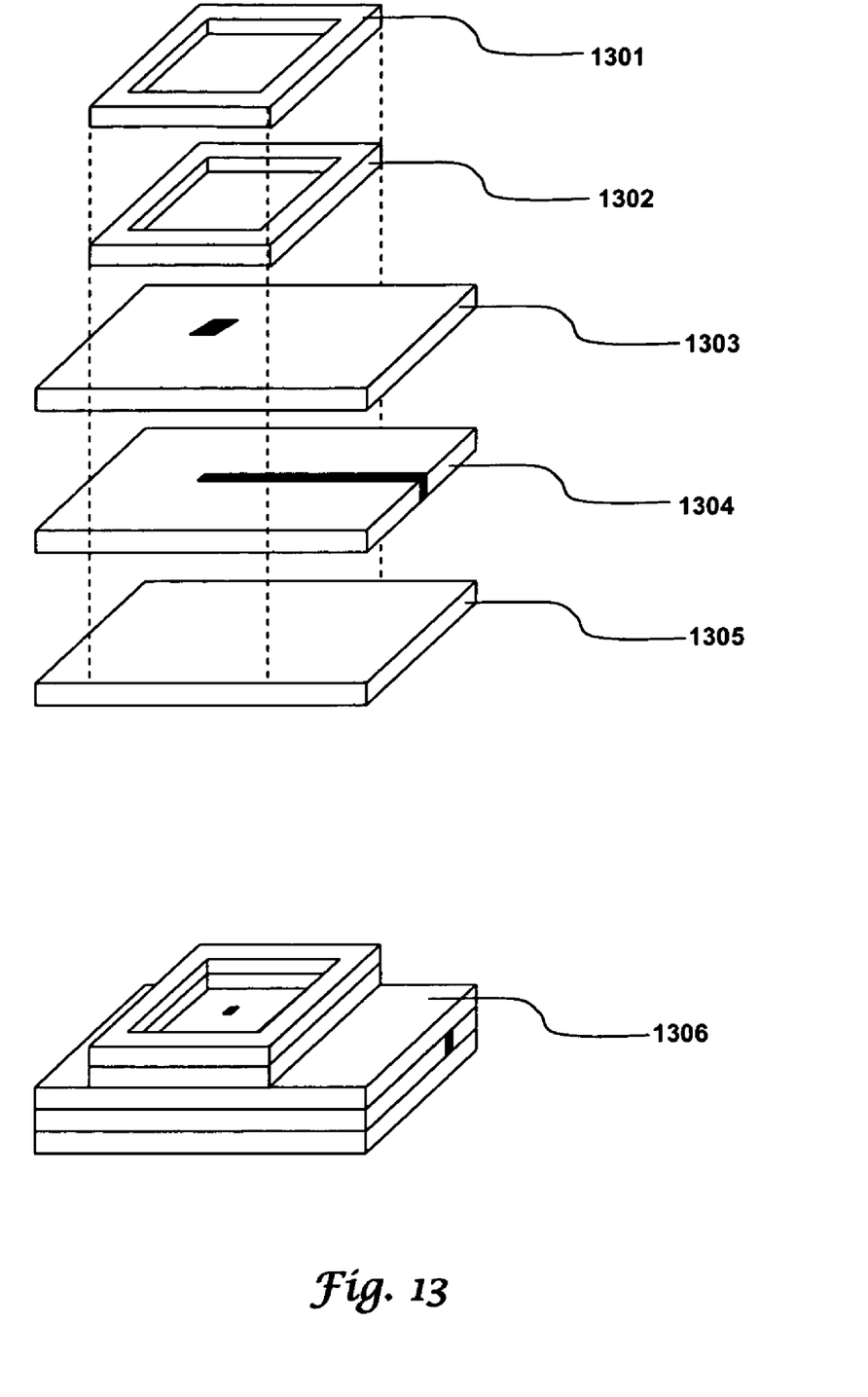
FIG. 13 illustrates forming a MLCC package with an air passage into the cavity.

FIG. 13 illustrates a forming a MLCC package with a passage in accordance with aspects of the embodiments. For illustrative purposes, the MLCC package has 5 layers although any number can be used. The first layer 1301 and the second layer 1302 will form a cavity. The third layer 1303 has a hole that can be aligned with the reference port of a pressure sensor. The fourth layer 1304 has a cut that will form an air passage. The fifth layer 1305 is blank. The five layers can be stacked and fired to form a MLCC package 1306 having a passage to the sensor lumen through which air can reach from the exterior. A pressure sensor die can be placed in the cavity such that the reference input and the hole align to thereby provide a reference to the backside of the sensor. The internal bond pads, internal interconnects, and exterior connection points are not shown. Also not shown is continuation of the channel 1304 to allow air or other reference media to pass through the sensor package to another sensor as shown in FIG. 10.

Figure 14:
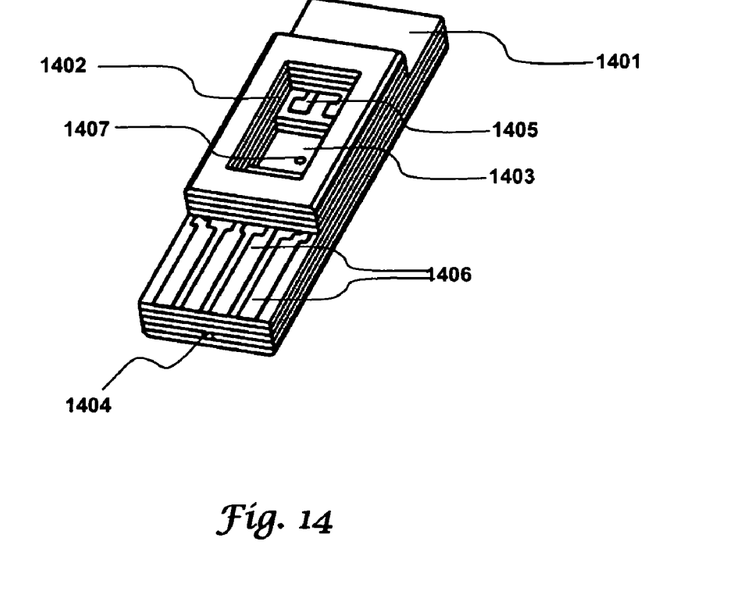
FIG. 14 illustrates a three dimensional view of another illustrative MLCC sensor assembly without a sensor yet positioned and attached into the cavity.

FIG. 14 illustrates a three dimensional view of an MLCC sensor assembly 1401 in accordance with aspects of the embodiments. The cavity 1402 is illustrated as a stepped cavity that has a lower cavity 1403 in which to locate and seal the sensor die. A hole 1407 can be seen in the base of the lower cavity 1403. The hole 1407 connects to a channel in a lower layer, with another hole 1404 being at the other end of this channel. The internal bond pads 1405 are electrically connected to the external connection points 1406.

Figure 15:
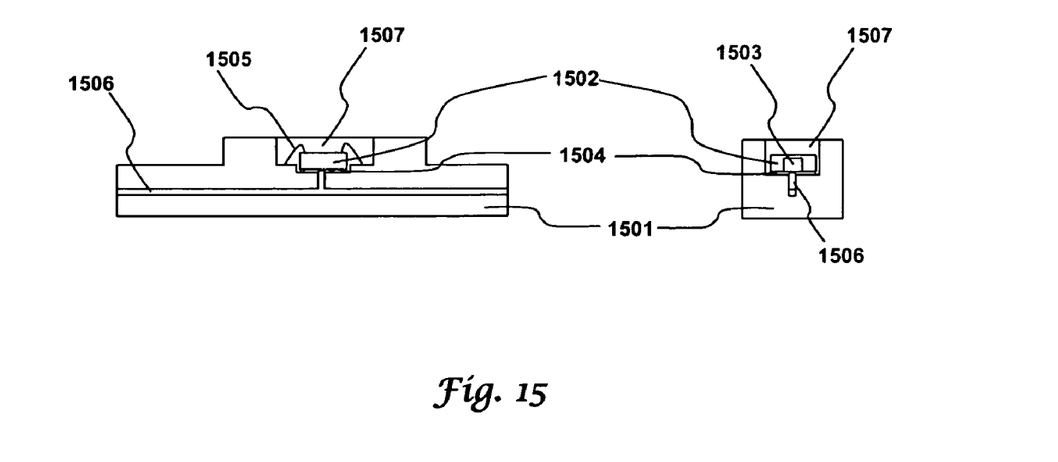
FIG. 15 illustrates two cut views of an illustrative MLCC sensor assembly that is similar to that shown in FIG. 14.

FIG. 15 illustrates two cut views of an MLCC sensor assembly 1501 in accordance with aspects of the embodiments. The cavity 1507 is illustrated as a stepped cavity that has a lower cavity. A channel 1506 passes completely through the MLCC sensor assembly 1501 as well as connecting to a hole in the cavity 1507 base. A sensor 1502 is sealed in the cavity 1507 using a die attach adhesive 1504 that bonds and seals the sensor 1502 to the MLCC. The amount and placement of sealant must be controlled so that the hole under the sensor 1502 remains open. The sensor 1502 has wire leads 1505 that electrically connect the sensor 1502 to internal bond pads. The sensor 1502 has a reference chamber 1503 that is positioned over the hole. A fluid, such as air, should be free to pass through the channel 1506 and into the reference chamber 1503.

It will be appreciated that variations of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

The embodiments of the invention in which an exclusive property or right is claimed are defined as follows. Having thus described the invention what is claimed is:

1. A system comprising:
   A multi-layer co-fired ceramic (MLCC) package comprising a cavity, at least one internal bond pad, at least one external connection point, and at least one internal interconnect wherein the at least one internal bond pad is positioned within the cavity, wherein the at least one external connection point is on an exterior of the MLCC package, and wherein the at least one internal interconnect provides an electrical connection between at least one of the at least one internal bond pad and at least one of the at least one external connection point;
   the MLCC package including two or more ceramic layers that are co-fired together, wherein the cavity is defined by at least some of the ceramic layers;
   a sensor positioned and attached within the cavity, and electrically connected to the at least one internal bond pad to form an MLCC sensor assembly; and
   a catheter comprising at least one lumen wherein at least one of the at least one lumen is a sensor lumen and wherein the MLCC sensor assembly is positioned within the sensor lumen.

2. The system of claim 1 further comprising a ribbon cable electrically connected to at least one of the at least one external connection point and passing through the sensor lumen.

3. The system of claim 1 further comprising an air passage that supplies a passageway from outside the MLCC package to the cavity and thereby provides a reference input to the pressure sensor.

4. The system of claim 1 wherein the MLCC package is a stepped MLCC package comprising at least one step and wherein each of the at least one external connection point is positioned on the at least one step.

5. The system of claim 4 further comprising a ribbon cable electrically connected to at least one of the at least one external connection point and passing through the sensor lumen.

6. The system of claim 1 further comprising:
a second MLCC sensor assembly positioned within the sensor lumen.

7. The system of claim 6 further comprising a ribbon cable electrically connected to at least one of the at least one external connection point of the MLCC sensor assembly and passing past the second MLCC sensor assembly and passing through the sensor lumen.

8. The system of claim 1 further comprising a sealant within the cavity and encapsulating the sensor.

9. A system comprising:
a pressure sensor;
a multi-layer co-fired ceramic (MLCC) package comprising a cavity, at least one internal bond pad, at least one external connection point, and at least one internal interconnect wherein the at least one internal bond pad is positioned within the cavity, wherein the at least one external connection point is on an exterior of the MLCC package, wherein the at least one internal interconnect provides an electrical connection between at least one of the at least one internal bond pad and at least one of the at least one external connection point, the MLCC package including two or more ceramic layers that are co-fired together, wherein the cavity is defined by at least some of the ceramic layers, and wherein the pressure sensor is attached within the cavity and electrically connected to the at least one internal bond pad;
a sealant within the cavity and encapsulating the pressure sensor to produce an MLCC sensor assembly; and
a catheter comprising at least one lumen wherein at least one of the at least one lumen is a sensor lumen and wherein the MLCC sensor assembly is positioned within the sensor lumen.

10. The system of claim 9 further comprising an air passage that supplies a passageway from outside the MLCC package to the cavity and thereby provides a reference input to the pressure sensor.

11. The system of claim 10 further comprising a ribbon cable electrically connected to at least one of the at least one external connection point and passing through the sensor lumen.

12. The system of claim 10 wherein the MLCC package is a stepped MLCC package comprising at least one step and wherein each of the at least one external connection point is positioned on the at least one step.

13. The system of claim 12 further comprising a ribbon cable electrically connected to at least one of the at least one external connection point and passing through the sensor lumen.

14. The system of claim 12 further comprising:
at least one additional MLCC sensor assembly positioned within the sensor lumen.

15. The system of claim 10 further comprising:
at least one additional MLCC sensor assembly positioned within the sensor lumen.

16. A method comprising:
producing a multi-layer co-fired ceramic (MLCC) package comprising a cavity, at least one internal bond pad, at least one external connection point, and at least one internal interconnect wherein the at least one internal bond pad is positioned within the cavity, wherein the at least one external connection point is on an exterior of the MLCC package, and wherein the at least one internal interconnect provides an electrical connection between at least one of the at least one internal bond pad and at least one of the at least one external connection point, the MLCC package including two or more ceramic layers that are co-fired together, wherein the cavity is defined by at least some of the ceramic layers;
attaching a sensor within the cavity and electrically connecting the sensor to the at least one internal bond pad;
encapsulating the sensor within the cavity to produce an MLCC sensor assembly; and
positioning the MLCC sensor assembly within a catheter lumen.

17. The system of claim 16 further comprising an air passage that supplies a passageway from outside the MLCC package to the cavity and thereby provides a reference input to the pressure sensor.

18. The method of claim 16 further comprising electrically connecting a ribbon cable to at least one of the at least one external connection point before positioning the MLCC sensor assembly within the catheter.

19. The method of claim 16 wherein the MLCC package is a stepped MLCC package comprising at least one step and wherein each of the at least one external connection point is positioned on the at least one step.

20. The method of claim 16 further comprising positioning an additional MLCC sensor assemblies within the sensor lumen.

* * * * *